United States Patent
Charles et al.

(10) Patent No.: US 9,668,475 B2
(45) Date of Patent: Jun. 6, 2017

(54) PHOTOCATALYTIC FILM FOR SOIL FUMIGATION

(75) Inventors: Patrick Charles, Sauvagnon (FR); Thierry Fouillet, Sauvagnon (FR)

(73) Assignee: ARKEMA FRANCE, Colombes (FR)

( * ) Notice: Subject to any disclaimer, the term of this patent is extended or adjusted under 35 U.S.C. 154(b) by 185 days.

(21) Appl. No.: 14/241,555

(22) PCT Filed: Aug. 31, 2012

(86) PCT No.: PCT/FR2012/051960
§ 371 (c)(1),
(2), (4) Date: Feb. 28, 2014

(87) PCT Pub. No.: WO2013/030513
PCT Pub. Date: Mar. 7, 2013

(65) Prior Publication Data
US 2014/0377007 A1 Dec. 25, 2014

(30) Foreign Application Priority Data
Sep. 1, 2011 (FR) ...................................... 11 57730

(51) Int. Cl.
*A01N 25/32* (2006.01)
*A01N 41/12* (2006.01)
(Continued)

(52) U.S. Cl.
CPC .............. *A01N 25/32* (2013.01); *A01G 11/00* (2013.01); *A01M 13/003* (2013.01);
(Continued)

(58) Field of Classification Search
CPC ........ A01N 25/32; A01N 25/00; A01N 41/12; A01N 41/00; A01G 11/00; A01M 13/003;
(Continued)

(56) References Cited

U.S. PATENT DOCUMENTS

RE28,883 E * 6/1976 Willdorf ........... B32B 17/10018
156/104
4,819,374 A 4/1989 Gemgnani
(Continued)

FOREIGN PATENT DOCUMENTS

EP 0 766 913 A1 4/1997
EP 1 460 109 A1 9/2004
(Continued)

OTHER PUBLICATIONS

Derwen-Acc-No. 1968-68034P, Methacrylate homopolymer solutions used as medical, BOFORS AB[BOFO], May 27, 1963, Basic Abstract.*
(Continued)

*Primary Examiner* — Christopher J Novosad
(74) *Attorney, Agent, or Firm* — RatnerPrestia

(57) ABSTRACT

The present invention relates to a photocatalytic film including at least one polymer layer (1) including at least one photocatalyst, said layer being pervious to both the vapors of at least one fumigating compound and ultraviolet radiation capable of activating the photocatalyst. The present invention also relates to a method for treatment by fumigation using said photocatalytic film and at least one fumigant.

23 Claims, 1 Drawing Sheet

(51) Int. Cl.
| | |
|---|---|
| *A01G 11/00* | (2006.01) |
| *A01M 13/00* | (2006.01) |
| *A01M 17/00* | (2006.01) |
| *A01M 21/04* | (2006.01) |
| *B01J 31/38* | (2006.01) |
| *B09C 1/08* | (2006.01) |
| *B32B 27/08* | (2006.01) |
| *B32B 27/18* | (2006.01) |
| *B32B 27/32* | (2006.01) |
| *B32B 27/36* | (2006.01) |
| *B32B 27/20* | (2006.01) |
| *B32B 27/34* | (2006.01) |
| *C08J 5/18* | (2006.01) |
| *C08F 10/02* | (2006.01) |

(52) U.S. Cl.
CPC ........ *A01M 17/002* (2013.01); *A01M 21/043* (2013.01); *A01N 41/12* (2013.01); *B01J 31/38* (2013.01); *B09C 1/08* (2013.01); *B32B 27/08* (2013.01); *B32B 27/18* (2013.01); *B32B 27/20* (2013.01); *B32B 27/32* (2013.01); *B32B 27/34* (2013.01); *B32B 27/36* (2013.01); *C08F 10/02* (2013.01); *C08J 5/18* (2013.01); *B01J 2231/70* (2013.01); *B32B 2250/40* (2013.01); *B32B 2264/102* (2013.01); *B32B 2307/7163* (2013.01); *B32B 2410/00* (2013.01); *C08J 2323/06* (2013.01); *C08J 2377/00* (2013.01)

(58) Field of Classification Search
CPC .... A01M 13/00; A01M 17/002; A01M 17/00; A01M 21/043; A01M 21/04; A01M 21/00; B01J 31/38; B01J 31/26; B01J 31/02; B09C 1/08; B09C 1/00; B32B 27/08; B32B 27/06; B32B 27/00; B32B 27/18; B32B 27/20; B32B 27/32; B32B 27/34; B32B 27/36; C08F 10/02; C08F 10/00; C08J 5/18; C08J 5/00
See application file for complete search history.

(56) References Cited

U.S. PATENT DOCUMENTS

| | | | |
|---|---|---|---|
| 5,011,698 A * | 4/1991 | Antoon, Jr. | A61L 15/18 206/524.6 |
| 5,391,609 A | 2/1995 | Knoerzer et al. | |
| 5,616,532 A * | 4/1997 | Heller | B01J 35/002 502/242 |
| 5,674,618 A | 10/1997 | Lee et al. | |
| 7,866,088 B1 | 1/2011 | Shahar | |
| 2004/0175288 A1* | 9/2004 | Horton, III | A61L 9/205 422/4 |
| 2005/0014433 A1* | 1/2005 | Langley | B32B 5/26 442/76 |
| 2005/0202236 A1 | 9/2005 | Busch et al. | |
| 2008/0044629 A1 | 2/2008 | Sabbagh | |
| 2009/0130158 A1 | 5/2009 | Dujardin et al. | |
| 2010/0112680 A1* | 5/2010 | Brockwell | A61B 5/07 435/287.9 |
| 2011/0162955 A1* | 7/2011 | Butzloff | B01J 21/063 204/157.15 |

FOREIGN PATENT DOCUMENTS

| | | |
|---|---|---|
| EP | 2 386 594 A2 | 9/2005 |
| EP | 1 609 816 A1 | 12/2005 |
| JP | 9 263502 | 10/1997 |
| JP | 2006316440 A * | 11/2006 |
| JP | 4692989 B2 * | 6/2011 |
| WO | WO 01/00716 A2 | 1/2001 |

OTHER PUBLICATIONS

International Search Report of PCT/FR2012/051960, With English Translation, Issued Oct. 31, 2012.

* cited by examiner

PHOTOCATALYTIC FILM FOR SOIL FUMIGATION

CROSS REFERENCE TO RELATED APPLICATIONS

This application is the U.S. National Phase application of PCT International Application No. PCT/FR2012/051960, filed Aug. 31, 2012, and claims priority to French Patent Application No. 1157730, filed Sep. 1, 2011, the disclosures of which are incorporated by reference in their entirety for all purposes.

FIELD OF THE INVENTION

The present invention relates to the field of soil fumigation, i.e. the treatment of soils or plant substrates (composts, peats, rockwool, etc.), in particular substrates intended for agriculture, for controlling nematodes, pathogenic fungi, weeds, harmful insects or bacteria.

BACKGROUND OF THE INVENTION

The fumigation technique is today widely used for the disinfection of soils or plant substrates, in particular those intended for intensive agriculture and in particular those intended for tree cultivation, for horticulture and for market gardening.

This fumigation technique uses at least one fumigant, generally a volatile pesticidal compound, which is introduced into the soil or the substrate to be treated, according to various techniques known to those skilled in the art, for example using colters, or nozzles for injection into the soil, or else by drip. This fumigation technique also comprises the use of at least one fumigant in the form of a gas or fog, above the soil or plant substrate to be treated.

The fumigant diffuses into the soil or more generally into the substrate to be disinfected, but also rises back up to the surface and can be dissipated into the atmosphere. Large amounts of fumigant can thus be lost, leading to a loss of efficiency of the product used. In addition, the fumigant thus dissipated into the atmosphere can be a nuisance or even toxic for farmers and the entourage in the immediate proximity of the crops and fields treated.

In order to overcome this drawback, it is common practice to cover the soil treated by fumigation with a polymer film which is impermeable to the vapors of the fumigant, as described, for example, in EP-A1-0 766 913. This gas-impermeable, plastic sheet prevents said fumigant from dispersing in the air above the soil or the substrate to be treated. In this way, there is a space between the soil or substrate and the polymer film, in which the fumigant vapors are concentrated, thus reinforcing the efficiency of said fumigant. Various types of films, such as polyethylene films, or films of SIF (semi-impermeable film), VIF (virtually impermeable film) or TIF (totally impermeable film) type, are today used during soil or substrate treatments by fumigation.

The films for disinfecting agricultural soils can be classified into two categories according to the duration of use:
a) Category 1: "Simple" Protection: These films are kept in place during the required duration of disinfection of the substrate to be treated, and are then removed before the substrate is used for growing. This category comprises two subcategories, depending on whether or not the films are assembled together by adhesive bonding:
  i) films put in place without adhesive bonding, film on film,
  ii) films of which the surface condition allows assembly of the strips by adhesive bonding in situ;
b) Category 2: Protection and Mulching: The films of this category first of all provide protection during the disinfection, and are then kept in place as mulching films.

The polymer films are advantageously placed on the soil or substrate before or after the treatment by fumigation, and left in place for the time necessary to allow effective control of nematodes, phytopathogenic fungi, weeds, harmful insects and other bacteria. After this treatment period, the duration of which greatly depends on the soils or substrates to be treated, on the climatic conditions, on the type of crop envisioned, and the like, the polymer films can be, where appropriate, removed or simply perforated, in order to allow the planting of crops.

The use of polymer films in fields has other advantages, such as increased soil temperature, in particular at the beginning of spring, fewer problems associated with the appearance of weeds, moisture content retention, a reduction in the number of certain insect pests, higher yields and a more efficient use of soil nutrients.

Most mulch films are generally black for weed killing, white for cooling, or clear for short-duration disinfections or for warming the soil. The temperature of the soil under a plastic mulch depends on the thermal properties (reflection, adsorption or transmittance) of the particular constituent material of the film, with respect to the entering solar radiation.

For example, black mulches retain moisture content and heat while at the same time preserving infestation by weeds. Black, the predominant color used in vegetable production, is an opaque absorber and a radiator. Black mulch absorbs most ultraviolet (UV), visible and infrared (IR) wavelengths of incident solar radiation and re-emits part of the absorbed energy in the form of thermal or infrared radiation. A large part of the solar energy absorbed by black plastic mulch is lost into the atmosphere by radiation and by forced convection.

On the other hand, transparent polymer films sparingly absorb solar radiation, but transmit from 85% to 95% of said radiation, with a relative transmittance which depends on the thickness and the degree of opacity of the film. The surface under these polymer mulches is generally covered with drops of condensed water. This water is transparent to the entering short-wave radiation, but is opaque to the leaving infrared thermal radiation, heat lost into the atmosphere from an uncovered soil due to infrared radiation, but which is retained by the transparent polymer mulch.

White films, for their part, can lead to a slight decrease in soil temperature compared to an uncovered soil, since they reflect, into the plant cover, most of the incident solar radiation. These mulches can be used to establish a crop when the soil temperatures are high, for instance in very sunny regions and where any reduction in soil temperature is beneficial.

There is therefore today a large amount of polymer films used in agriculture. The use of such films could be coupled with the use of fumigant, as previously indicated. However, when the polymer film is withdrawn or perforated, the fumigant still present in the form of vapors between the soil and said film escapes into the atmosphere and can thus be harmful to the environment, without mentioning the operators who are also widely exposed to said vapors of said fumigant.

In order to avoid exposure of the operators to the toxic and/or malodorous vapors of fumigants, the wearing of filtering masks or of specific respiratory apparatuses has been envisioned. Their use is, however, inconvenient and it is often noted that operators do not use these devices, which are nevertheless often necessary.

In addition, fumigants are in most cases toxic products, the inhalation of which by operators and the dissipation of which into the atmosphere should be avoided. Such is the case, for example, of methyl bromide which is today used less and less frequently because of its toxicity. Moreover, methyl bromide is now prohibited by the Montreal protocol, since this fumigant is considered to be a substance capable of destroying the stratospheric ozone layer. Patent application JP 9-263502 proposes another solution for avoiding the dispersion of methyl bromide into the atmosphere. This solution consists in using a multilayer photocatalytic film, an upper layer permeable to solar radiation, and a lower layer permeable to the fumigant used. Particles of titanium dioxide, acting as a photocatalyst, are deposited according to a "spray/coating" process on the lower layer, and then covered by lamination and sealing of the upper layer.

However, the photocatalytic films presented in said patent application dating from 1996 are not entirely satisfactory, and have not, thus far, been marketed. The preparation thereof on an industrial scale appears to be difficult to implement, and these films especially would not exhibit the mechanical properties required by the standards relating to films for the disinfection of agricultural soils (AFNOR NF T 54-195), in particular with regard to the specifications relating to delamination, tensile strength, tearing, slow perforation and bonding ability of the film.

In addition, spray-deposited titanium dioxide ($TiO_2$) particles have the drawback of being able to be washed away by the condensation water running on or under the films. Moreover, the spray-coating technique imposes relatively low manufacturing rates, thus leading to a high final manufacturing cost for this type of structure.

More specifically, the examples of catalytic films described in patent application JP 9-263502 are films composed of a first layer of poly(vinylidene chloride) or of nylon and of a second layer of poly(ethylene) or of poly(vinyl chloride). A layer of ultrafine particles of titanium dioxide is deposited between these two layers. The whole assembly is thermosealed on at least part of the surface of the film. Not only does this film therefore appear to be very difficult to prepare, but it also requires a difficult thermosealing operation in the presence of the photocatalyst particles.

Another example presented in patent application JP 9-263502 shows a bilayer film in which the lower layer consist of poly(tetrafluoroethylene) comprising ultrafine particles of titanium dioxide (up to a quantitative ratio of 1:9). The nature of the other constituent polymer film of the bilayer is not indicated.

The compatibility of the titanium particles with the poly(tetrafluoroethylene) does not appear to be optimal (the film does not therefore appear to be very solid for the uses envisioned) since it is indicated, in another example of this same patent application, that it is preferable to use a flocculant ("bulking agent"), such as talc, aluminum hydroxide, calcium carbonate or porous silica, to obtain a better distribution of the photocatalyst particles within the polymer matrix.

Finally, the films described in patent application JP 9-263502 do not work with colored films since they do not take into account the colorants of which they are composed and which have the ability to adsorb the ultraviolet radiation required for the catalytic activity of the titanium dioxide particles.

All these examples show that the manufacturing of photocatalytic films is not easy and still remains today difficult to industrialize. There is, consequently, a need for photocatalytic films which can be used in the fumigation field and which are therefore impermeable to fumigant vapors, and which have a photocatalytic activity allowing efficient photocatalysis of fumigants. Such films should be easily industrializable and should exhibit a mechanical strength suitable for the uses envisioned, in order to be able to be easily handled and spread out over the soils or substrates to be treated by fumigation.

SUMMARY OF THE INVENTION

A first aspect of the present invention is a photocatalytic film comprising at least one polymer layer (1), said layer comprising at least one photocatalyst, and being both permeable to the vapors of at least one fumigating compound and permeable to ultraviolet radiation capable of activating the photocatalyst.

According to another aspect, the present invention relates to the process for preparing a photocatalytic film, according to any method known to those skilled in the art for preparing films from master-batches, said process comprising at least the following steps: a) preparing granules of a master-batch from a first matrix of at least one polymer A as previously defined and from nanometric particles, optionally in the form of granulated material, aggregates or agglomerates, of at least one photocatalyst, the median diameter of which is as previously defined, said particles being present in an amount of between 10% by weight and 50% by weight relative to the total weight of the master-batch, by mixing said first matrix and said particles, then extrusion, for example, with a twin-screw extruder or a Buss coblender; and b) preparing a photocatalytic film from the granules of the master-batch obtained in step a) by incorporating an amount of between approximately 5% and approximately 50%, preferably between approximately 5% and approximately 30% by weight, relative to the final polymer prepared, of said granules obtained in step a) into a second polymer matrix (of nature identical to or different than, preferably identical to, the first polymer matrix) which is molten or in the form of granules and then melted.

Another subject of the present invention is a process for fumigating a soil, a cultivatable substrate or an item, comprising at least the following steps:
a) application in said soil, substrate or item, and/or at the surface of said soil, substrate or item, of at least one fumigant, as has just been defined;
b) total or partial coverage of said soil, substrate or item with a photocatalytic film, as previously defined, before or after step a);
c) exposure of said photocatalytic film to ultraviolet radiation, for a period of time which can range from a few days to several weeks; and
d) optional total or partial removal or simple perforation of said photocatalytic film.

A subject of the invention is also a fumigation treatment kit comprising at least one photocatalytic film as previously described, and at least one fumigant, preferably at least one sulfur-containing volatile organic compound, preferably of formula (I) or of formula (I'), said fumigant more preferably being dimethyl disulfide.

DETAILED DESCRIPTION

Figure 1:
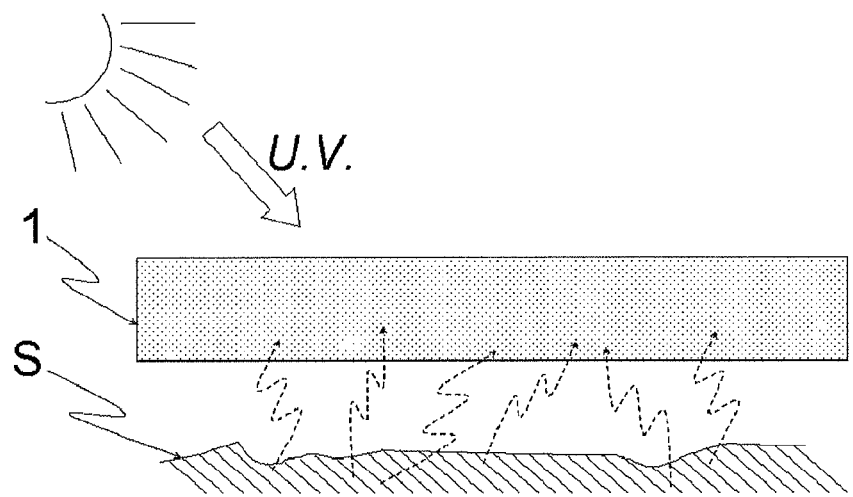
FIG. 1 represents diagrammatically a film for fumigation comprising a first polymer layer loaded with photocatalyst.

A first aspect of the present invention is a photocatalytic film comprising at least one polymer layer (1), said layer comprising at least one photocatalyst, and being both permeable to the vapors of at least one fumigating compound and permeable to ultraviolet radiation capable of activating the photocatalyst.

The photocatalyst of the film according to the invention is a catalyst capable of degrading said at least one fumigant by photocatalysis, as described later in the present description.

The film according to the present invention must be permeable to ultraviolet radiation in order to allow the activation of the photocatalyst and the degradation of said at least one fumigant. The film according to the present invention may also optionally be permeable to visible radiation, i.e. be transparent, or more or less opaque. As will be seen later, the film of the present invention may also be partially or totally opaque to visible radiation, or even be colored, the choice of the transparency, of the opacity and of the color of the film depending on the use envisioned for the film of the present invention. In each of these variants, it should be understood that the film of the present invention is always permeable to ultraviolet radiation.

The term "ultraviolet radiation" is intended to mean radiation having a wavelength generally between approximately 280 nm and approximately 400 nm. The term "visible radiation" is intended to mean radiation having a wavelength generally between approximately 400 nm and approximately 800 nm.

The term "permeable to ultraviolet radiation" and the term "permeable to visible radiation" are intended to mean a polymer layer allowing at least a transmittance of approximately 5%, preferably approximately at least 10%, more preferably approximately at least 20%, of the ultraviolet radiation and of the visible radiation, respectively. The transmittance is the ratio of the flux of photons transmitted relative to the flux of incident photons, the flux being measured by UV or visible spectrophotometry in the wavelength range under consideration.

The term "permeable to the vapors of at least one fumigating compound" is intended to mean the permeability defined according to the NF T 54-195 standard, with a permeability value of at least (i.e. greater than or equal to) 0.2 g/m²·hour. Conversely, the impermeability is to fumigant vapors corresponds to a permeability strictly less than 0.2 g/m²·hour.

The polymer layer (1) is advantageously a polymer film comprising at least one polymer A preferably chosen from polyolefins and polyesters. Biobased and/or biodegradable polyolefins and polyesters are quite particularly preferred.

For the purpose of the present invention, the term "polyolefin" is intended to mean a random or block polymer or copolymer resulting from the polymerization, or respectively from the copolymerization, of monomers which are olefins, preferably chosen from ethylene, propylene, 1-butene, and the like, and also mixtures thereof.

By way of examples of polyolefins, mention may be made of:

propylene-based polymers, such as propylene homopolymers, copolymers of propylene with ethylene and/or an olefin comprising from 4 to 10 carbon atoms (for example, butene, pentene, hexene, and the like), heterophasic polypropylenes or mixtures thereof, it being possible for these polymers to be obtained by any process known to those skilled in the art, e.g. in suspension or in the gas phase with catalysts of Ziegler-Natta or metallocene type;

polyethylenes chosen from ethylene homopolymers or copolymers comprising at least 50 mol % of ethylene and one or more comonomers.

According to one preferred embodiment, the polymer layer (1) consists of a polymer A which is polyethylene obtained by polymerization, preferably homopolymerization, of ethylene. As a variant, when the polymer A is a copolymer, the comonomer is preferably an α-olefin. The preferred α-olefins have from 2 to 30 carbon atoms.

By way of α-olefin, mention may be made of propylene, 1-butene, 1-pentene, 3-methyl-1-butene, 1-hexene, 4-methyl-1-pentene, 3-methyl-1-pentene, 1-octene, 1-decene, 1-dodecene, 1-tetradecene, 1-hexadecene, 1-octadecene, 1-eicosene, 1-docosene, 1-tetracosene, 1-hexacosene, 1-octacosene and 1-triacontene.

By way of other comonomers of the copolymers A, mention may also be made of:

dienes, such as, for example, 1,4-hexadiene, ethylidene-norbornene, or butadiene, unsaturated carboxylic acid esters, such as, for example, alkyl acrylates or alkyl methacrylates grouped together under the term "alkyl (meth)acrylates", it being possible for the alkyl chains of these (meth)acrylates to contain up to 30 carbon atoms, with, as examples of alkyl chains: methyl, ethyl, propyl, n-butyl, sec-butyl, isobutyl, tert-butyl, pentyl, hexyl, heptyl, octyl, 2-ethylhexyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, and triacontyl, methyl, ethyl and butyl (meth)acrylates being preferred, unsaturated carboxylic acids and salts thereof, for example acrylic acid or methacrylic acid and the salts of these same acids, vinyl esters of carboxylic acids, among which mention may be made of vinyl acetate, vinyl versatate, vinyl propionate, vinyl butyrate and vinyl maleate, vinyl acetate being quite particularly preferred.

The synthesis of these polymers and copolymers can be carried out by any process known per se, and for example by high-pressure free-radical polymerization or copolymerization (autoclave or tubular process) or according to two main methods in the case of linear copolymers: the solution method and the fluidized bed method (in the gas phase). In the latter case, the catalyst used may be of Ziegler-Natta or metallocene type, or else of Phillips type. It is of course possible to use mixtures of two or more of the polyolefins and/or copolyolefins described above.

Among the polyesters that can be used as polymer A, preference is given to biobased or biodegradable polyesters, and more preferably those chosen from:
- polylactides: for example, polymers and copolymers of lactic acid (PLA) or else polymers and copolymers of glycolic acid (PGA);
- homopolymeric or copolymeric poly(hydroxyalkanoates) (or PHA): for example, poly(hydroxybutyrates) (PHB), copolymers of hydroxybutyrate-valerate (PHBV), for example poly(3-hydroxybutyrate)-poly(3-hydroxyvalerate)s, copolymers of hydroxybutyrate-hexanoate (PHBHx), and hydroxybutyrate-hexanoate copolymers (PHBO);
- poly(alkylene succinates) (PAS), for instance polyethylene succinate) or PES, and polybutylene succinate) or PBS;
- other polymers, such as poly(butylene succinate-adipate) or PBSA, poly(butylene adipate-terephthalate) or PBAT, poly(caprolactone) or PCL, or poly(trimethylene terephthalate) or PTT;
- thermoplastic starch (TPS) or starch-based mixtures.

It is of course possible to use mixtures of two or more of the polyesters and copolyesters described above.

The term "biobased" or "renewable" applies to a natural source, the stock of which can be reconstituted over a short period on the human scale, the source having to be renewed as quickly as it is consumed. In the context of the present invention, the biobased materials correspond to organic materials in which the carbon atoms come from non-fossil sources (cf. ASTM 6866: Biobased Materials—organic materials in which the carbon comes from contemporary (non-fossil) biological sources).

The term "biodegradable" applies to a material which can be degraded by microorganisms. The result of this degradation is mainly the formation of water, of carbon dioxide and/or of methane, and also possibly of by-products (residues, new biomass) which are not toxic to the environment.

For the needs of the present invention, use is advantageously made of polyolefins chosen from polypropylene, polyethylene, copolymers of ethylene and of an α-olefin, ethylene/alkyl (meth)acrylate copolymers, and ethylene/carboxylic acid vinyl ester copolymers.

The polymer layer (1), of which polyethylene is particularly preferably the main constituent, and advantageously the only constituent (polymer A), also comprises at least one photocatalyst capable of degrading by photocatalysis said at least one fumigant intended for treating the soil or plant substrate. The expression "capable of degrading by photocatalysis said at least one fumigant" means that the photocatalytic film, under the action of ultraviolet radiation, degrades at least a part of the fumigant(s) intended for treating the soil or the plant substrate covered with said photocatalytic film. The degree of degradation depends, of course, on the amount of ultraviolet radiation, and is evaluated by comparison with a film of the same nature but which is not photocatalytic, i.e. does not comprise photocatalyst particles. Such measurements are presented in the examples given later in the description of the invention.

The photocatalytic effect corresponds to the photocatalytic effect well known to those skilled in the art and uses "electron-hole" pairs photogenerated when the film is subjected to radiation having a wavelength of less than 400 nm. These "electron-hole" pairs react with the oxygen and the moisture in ambient air and the hydroxyl groups or organic products adsorbed at the surface of the photocatalyst particles present in the film, to give radicals, in particular highly oxidizing superoxide and hydroxyl radicals. The photocatalysis therefore makes it possible to decompose organic molecules at the surface of the photocatalyst particles, through the formation of free radicals which will initiate breaking of the covalent bonds of said organic molecules.

In order to confer the photocatalytic effect on the films of the present invention, the photocatalyst particles included in said film have an average particle size of between 0.5 nm and 200 nm, preferably between 0.5 nm and 180 nm, more preferably between 0.5 nm and 100 nm, advantageously between 1 nm and 50 nm, particularly between 10 nm and 40 nm and more particularly between 15 nm and 30 nm.

The average particle size (median diameter of the photocatalyst particles) is measured by transmission electron microscopy (TEM) using a Philips CM200 apparatus (200 kV, LaB6 filament, point-by-point resolution of 0.27 nm). Direct observation of the images on a screen is possible through the use of a high-resolution CCD camera (11 Mpixels—Gatan Orius 832 model). The median diameters of at least 500 photocatalyst particles are statistically measured and their particle size distribution by number is established. The average particle size is defined as the average value of all the particles measured.

Since the photocatalyst particles are ultrafine particles (of nanometric size), their use may be difficult and may present risks of toxicity to users. For these reasons, inter alia, the nanometric photocatalyst particles may be commercially available in the form of granulated material, of aggregates or of agglomerates, the size of which can vary in wide proportions, for example between a few hundred nanometers to a few micrometers, or even a few tens of micrometers, for example between approximately 200 nm and 1 μm. This granulation material or these aggregates or agglomerates of photocatalytic nanometric particles have the same photocatalytic properties as the nanometric particles of which they are composed. For this reason, this granulated material and these aggregates and agglomerates of nanometric particles should not be confused with the particles of higher median diameter (greater than 200 nm) and which are generally used as pigment and/or agents for protecting against ultraviolet radiation, as will be seen later in the present description.

Said at least one photocatalyst present in the photocatalytic film of the present invention can be chosen from the photocatalysts known to those skilled in the art, and which have an average particle size as defined above (0.5 nm to 200 nm), the most commonly used being oxides, sulfides or carbides of metals having semi-conductive properties.

Advantageously, and by way of nonlimiting examples, the photocatalyst present in the film according to the present invention is chosen from titanium dioxide, silicon dioxide, zinc oxide, tungsten trioxide, silicon carbide, iron II oxide or iron III oxide, cerium dioxide, zirconium dioxide, tin dioxide, zinc sulfide, cadmium sulfide, silicon carbide, and the like, and also mixtures of two or more of them in any proportions.

Preferably, the photocatalyst is photocatalytic nanometric titanium dioxide, owing to its performance levels and its cost. Titanium dioxide exists in three crystalline forms, which are brookite, anatase and rutile, but only the anatase and rutile structures have photocatalytic properties and are of use in the film of the present invention. The anatase structure is more effective than the rutile structure; however, anatase/rutile mixtures (preferably approximately 70/30 to approximately 80/20 by weight respectively) exhibit better results in terms of photocatalysis than one or other of the structures alone.

According to one particularly preferred embodiment of the films of the present invention, the photocatalyst is the nanometric titanium dioxide sold by the company Evonik under the name Aeroxide® TiO$_2$ P 25. Aeroxide® TiO$_2$ P 25 is a white powder composed of the two crystalline forms of TiO$_2$, the anatase form which makes up more than 70% (by weight) and the rutile form, the crystals of which measure on average 21 nm in terms of average diameter and which have a specific surface area of 35 m$^2$/g to 65 m$^2$/g. It is also possible to use, as previously indicated, granulated material, aggregates or agglomerates of nanometric TiO$_2$ particles, and in particular photocatalytic TiO$_2$ particles in the form of granulated material, and especially that sold by Evonik under the name Aeroperl® P25/20, the granulated material of which has an average size of 0.25 µm and is made up of primary photocatalytic TiO$_2$ particles having a median diameter of approximately 20 nm.

As previously indicated, only TiO$_2$, in its rutile and anatase crystalline forms, exhibits photocatalytic activity. Since the anatase form is much more active than the rutile form, it is virtually the only one used for this application. TiO$_2$ in amorphous form does not have photocatalytic activity. TiO$_2$ is partially crystalline in anatase or rutile crystalline form or in the form of a mixture of anatase and rutile with a degree of crystallization preferably of at least 25%, preferably of at least 30%, for example between approximately 30% and 80% by weight relative to the total weight of TiO$_2$. The degree of crystallization and the nature of the crystalline phase are measured by X-ray diffraction (XRD), according to the techniques known to those skilled in the art. The degree of crystallization represents the amount by weight of crystalline TiO$_2$ relative to the total amount by weight of TiO$_2$ in the film. For the TiO$_2$ particles present in the film, preference is quite particularly given to those of which the nature of the crystalline phase is predominantly the anatase crystalline form. The term "predominantly" means that the anatase content of the TiO$_2$ particles is greater than 50% by weight, preferably greater than 60% by weight relative to the total weight of TiO$_2$ particles. Preferably, the TiO$_2$ particles used in the films of the present invention have an anatase content greater than or equal to 70%, more preferably greater than or equal to 80%.

It is of course possible to use one or more of the photocatalysts, described above, in doped form, doped with any type of dope known to those skilled in the art, for instance nitrogen, chromium, manganese, iron, platinum, and the like. It is also possible to combine these doped or non-doped photocatalysts with other semiconductors which absorb in the visible radiation range, for example cadmium sulfide (CdS), bismuth sulfide (Bi$_2$S$_3$), or tungsten trioxide (WO$_3$), and the like.

The amount of photocatalyst included in the polymer layer (1) can vary in large proportions, in particular according to the desired effect, the thickness and the nature of the film. As a general rule, the amount of photocatalyst is between 0.1% and 30% by weight of photocatalyst relative to the total weight of the polymer layer (1), preferably from 0.1% to 20% by weight, more preferably from 0.1% to 10% by weight of photocatalyst relative to the total weight of the polymer layer (1).

The incorporation of photocatalyst into the polymer matrix (1) can be carried out according to any means known to those skilled in the art for incorporating inorganic fillers into a polymer matrix. It is, however, preferred to carry out said incorporation using a master-batch, this being a technique which allows the distribution of the photocatalyst in the polymer matrix to be as homogeneous as possible. The photocatalyst concentration in the polymer matrix for this master-batch can range from 10% by weight to 50% by weight of photocatalyst relative to the total weight of the polymer matrix comprising said photocatalyst. A polymer/photocatalyst master-batch in which the photocatalyst is optimally dispersed on the nanometric scale in the polymer matrix is then obtained.

Thus, according to another aspect, the present invention relates to the process for preparing a photocatalytic film, according to any method known to those skilled in the art for preparing films from master-batches, said process comprising at least the following steps:

a) preparing granules of a master-batch from a first matrix of at least one polymer A as previously defined and from nanometric particles, optionally in the form of granulated material, aggregates or agglomerates, of at least one photocatalyst, the median diameter of which is as previously defined, said particles being present in an amount of between 10% by weight and 50% by weight relative to the total weight of the master-batch, by mixing said first matrix and said particles, then extrusion, for example, with a twin-screw extruder or a Buss coblender; and b) preparing a photocatalytic film from the granules of the master-batch obtained in step a) by incorporating an amount of between approximately 5% and approximately 50%, preferably between approximately 5% and approximately 30% by weight, relative to the final polymer prepared, of said granules obtained in step a) into a second polymer matrix (of nature identical to or different than, preferably identical to, the first polymer matrix) which is molten or in the form of granules and then melted.

The process described above allows the incorporation of an inorganic filler, in the form of granules, directly with the granules of polymer of the film to be manufactured, without modifying the extrusion line normally used (i.e. during the preparation of a film without the addition of photocatalyst particles), while at the same time providing a uniform distribution of said inorganic filler in this polymer matrix.

The thickness of the polymer layer (1) can vary in large proportions. However, the polymer layer (1) must be sufficiently thick to confer acceptable mechanical strength on the film according to the invention, and its thickness must not be too great, so as not to stiffen said film, so that it remains easy to handle.

In addition, the thickness of the polymer layer (1) depends on its concentration of photocatalytic filler which is intimately linked thereto. Indeed, by adjusting at least one of these two parameters (thickness and/or amount of photocatalyst), it is possible to control the degradation kinetics of the fumigant according to the climatic and edaphic conditions, such as the amount of sunshine, the moisture content, and the like.

Thus, by way of example, the thickness of the polymer layer (1) can be advantageously between approximately 5 µm and approximately 100 µm, preferably between 5 µm and 75 µm, preferably between 5 µm and 60 µm and more preferably between 5 µm and 50 µm.

According to one preferred embodiment, the thickness of the polymer layer (1) of the photocatalytic films is between 5 µm and 50 µm and the photocatalyst content is between 0.05% and 10%, preferably between 0.1% and 6% and more preferably between 1% and 3% by weight relative to the total weight of the polymer layer (1).

Yet another advantage of the photocatalytic film is that the polymer layer (1) preferably comprises a uniform and homogeneous distribution of photocatalyst particles over the entire thickness of the polymer. Thus, the photocatalytic effect is greatly improved compared with the photocatalytic films known from the prior art, and in particular that disclosed in patent JP 9-263502, in which only a fine layer of photocatalyst is deposited on the polymer film.

Without being bound by theory, the photocatalytic film of the invention acts, on the contrary, as an actual fumigant photocatalysis reactor, which consequently makes it possible to achieve the desired effect of virtually total photodegradation of said fumigant, thus avoiding potentially toxic and/or nauseating gas emissions when the polymer films are removed or pierced.

According to one variant, the photocatalytic film of the present invention is a multilayer photocatalytic film comprising:
a) at least one polymer layer (1) as previously defined, and
b) at least one layer of a second polymer film (2) impermeable to the vapors of said at least one fumigant and permeable to ultraviolet radiation.

More particularly, the polymer layer (2) is a polymer film comprising at least one polymer impermeable (i.e. having a permeability of less than 0.2 g/g/m²·hour) to fumigant(s) and permeable to ultraviolet radiation and optionally to visible radiation.

According to one particularly advantageous embodiment, the polymer layer (2) is chosen from nitrogenous and/or oxygen-containing polar resins, for example from polyamides, copolyamides, saponified copolymers of vinyl acetate and of ethylene (EVOH), polyesters and copolyesters, for example polyglycolic acid (PGA), thermoplastic starches and mixtures of two or more of them in any proportions.

For the purpose of the present invention, the term "polyamide" is intended to mean a polymer or copolymer comprising the products of condensation:
- of one or more amino acids, such as aminocaproic, 7-aminoheptanoic, 11-amino-undecanoic and/or 12-aminododecanoic acids;
- of one or more lactams, such as caprolactam, enantholactam and/or lauryllactam;
- of one or more diamines, optionally in salt form, such as hexamethylenediamine, dodecamethylenediamine, metaxylylenediamine, bis-para-aminocyclohexylmethane and/or trimethylhexamethylenediamine, with one or more diacids, for example chosen from isophthalic acid, terephthalic acid, adipic acid, azelaic acid, suberic acid, sebacic acid and dodecanedicarboxylic acid;
- or of mixtures of these monomers resulting in copolyamides.

It is possible to use mixtures of polyamide and/or copolyamides.

According to one preferred embodiment, the polymer used for the layer (2) of the film according to the invention is polyamide-6 or polyamide-6,6. According to another preferred embodiment, the polymer used for the layer (2) of the film according to the invention is a saponified copolymer of vinyl acetate and of ethylene (EVOH).

As for the polymer layer (1), the thickness of the polymer layer (2) can vary in large proportions. The polymer layer (2) must, however, be sufficiently thick to be impermeable to the vapors of the fumigant(s), and its thickness must not be too great so as not to needlessly stiffen the multilayer film, which must remain easy to handle.

By way of example, the thickness of the polymer layer (2) could be advantageously between 2 µm and 25 µm, preferably between 2 µm and 15 µm and more preferably between 2 µm and 10 µm. The present invention also comprises the photocatalytic films in which the polymer layer (2) is composed of several layers, for example PA6/EVOH/PA6 or PA6/PE/PA6.

The films according to the present invention also exhibit a mechanical strength which is entirely appropriate for manipulation on the land, said mechanical strength materializing through much easier handling. In particular, the films do not pierce and do not tear, even when the film placed on the soil is trodden on by the feet of users, handlers, farmers and the like.

By comparison with a film not comprising a polymer layer (2) which is a layer acting as a barrier to gases, for example when the film is a polyethylene film alone, the bilayer film comprising a polymer layer (1) and a polymer layer (2), such as they have been described, makes it possible to reduce the initial effective amount of fumigant, while at the same time having the same biological efficacy.

In one preferred embodiment, the present invention relates to a film consisting of at least one photocatalytic polyolefin layer (1) and at least one polyamide and/or EVOH layer (2) which is placed on a soil or an agricultural substrate into which or onto which at least one fumigant is injected.

In general, and in most cases, the polymers of the layer (1) and of the layer (2) are not compatible, i.e. the two films have only a moderate-to-low affinity toward one another, so that they can be assembled in the form of a bilayer film.

It is in fact known that certain polymers of different natures are only slightly compatible with one another, and it is often difficult to make them interlinked. This is in particular the case with films comprising a layer based on polyolefin(s) and a layer based on polyamide(s) or on EVOH.

Two possible methods can be used to overcome this drawback and to improve the adhesion between the layer (1) and the layer (2):
a) use of a compatibilizing agent, known to those skilled in the art, in the layer (1) and/or the layer (2), preferably in the layer (1), and/or
b) use of a "compatibility" or "coupling" layer (C), which can be understood to be a coextrusion tie, between the layers (1) and (2).

For example, when the film according to the invention is a bilayer in which the layer (1) is a "simple" polyolefin copolymer film (without compatibilizing agent) and the layer (2) is polyamide, the adhesion between the two layers is approximately equal to zero. On the other hand, when the bilayer consists of a polyolefin copolymer film (1) comprising a compatibilizing agent and a polyamide layer (2), the adhesion between the layer (1) and the layer (2), without using a tie between these layers, is greatly increased and generally reaches values ranging from approximately 4 to approximately 10 N/15 mm.

The adhesion tests between the various constituent layers of the films according to the present invention are carried out by peeling measurement at 180° C., with a linear speed of 20 mm/min on a film width of 15 mm.

In the rest of the present invention, it is considered that the various constituent layers of a film according to the present invention are "compatible" as long as the peeling test measurement described above gives a value of adhesion between two layers of at least 1 N/15 mm, preferably of at least 2 N/15 mm, more preferably of at least 3 N/15 mm and advantageously of at least 4 N/15 mm.

As regards method a), in the case where the polymer (1) is a polyolefin, the compatibilizing agents or the coextrusion ties are advantageously chosen from the polyolefins below comprising an additional monomer X:

propylene-based polymers, chosen from homopolymeric propylenes, copolymers of propylene with ethylene or a monomer comprising from 4 to 10 carbon atoms (for example butene, pentene, hexene, and the like), heterophasic polypropylenes or mixtures thereof, it being possible for the synthesis of these polymers to be carried out by any process known to those skilled in the art (for example in suspension, or in the gas phase with catalysts of Ziegler-Natta or metallocene type);

polyethylenes chosen from ethylene homopolymers or copolymers comprising at least 50 mol % of ethylene and one or more other comonomers; when the comonomer of the copolymer is an α-olefin, α-olefins having from 2 to 30 carbon atoms are preferred, it being understood that as second monomer, mention may be made of those chosen from:

dienes, for example 1,4-hexadiene, ethylidene norbornene, butadiene;

unsaturated carboxylic acid esters, such as, for example, alkyl acrylates or alkyl methacrylates, grouped together under the term alkyl (meth)acrylates, it being possible for the alkyl chains of these (meth)acrylates to have up to 30 carbon atoms, and among these alkyl chains, mention may be made of methyl, ethyl, propyl, n-butyl, sec-butyl, isobutyl, tert-butyl, pentyl, hexyl, heptyl, octyl, 2-ethylhexyl, nonyl, decyl, undecyl, dodecyl, tridecyl, tetradecyl, pentadecyl, hexadecyl, heptadecyl, octadecyl, nonadecyl, eicosyl, hencosyl, docosyl, tricosyl, tetracosyl, pentacosyl, hexacosyl, heptacosyl, octacosyl and nonacosyl chains, the preferred unsaturated carboxylic acid esters being methyl, ethyl and butyl (meth)acrylates;

vinyl esters of carboxylic acids, among which mention may be made of vinyl acetate, vinyl versatate, vinyl propionate, vinyl butyrate or vinyl maleate, preferably vinyl acetate.

The polyolefins listed above result from copolymerization with at least one unsaturated additional functional monomer X chosen from unsaturated carboxylic acid anhydrides, unsaturated dicarboxylic acid anhydrides, unsaturated carboxylic acids and unsaturated epoxides.

More specifically, as monomer X, mention may be made of:

unsaturated epoxides, for example aliphatic glycidyl esters and ethers, such as allyl glycidyl ether, vinyl glycidyl ether, glycidyl maleate and/or itaconate, glycidyl acrylate and/or methacrylate, but also alicyclic glycidyl esters and/or ethers, such as 2-cyclohexene-1-glycidyl ether, cyclohexene-4,5-diglycidyl carboxylate, cyclohexene-4-glycidyl carboxylate, 5-norbornene-2-methyl-2-glycidyl carboxylate and/or endo-cis-bicyclo(2,2,1)-5-heptene-2,3-diglycidyl dicarboxylate, glycidyl methacrylate being quite particularly preferred;

carboxylic acid and/or dicarboxylic acid anhydrides, e.g. chosen from maleic, itaconic, citraconic, allyl succinic, cyclohex-4-ene-1,2-dicarboxylic, 4-methylenecyclohex-4-ene-1,2-dicarboxylic, bicyclo[2,2,1]hept-5-ene-2,3-dicarboxylic and methylbicyclo[2,2,1]hept-5-ene-2,2-dicarboxylic anhydrides, maleic anhydride being quite particularly preferred.

In the latter case, the copolymers resulting from copolymerization with at least one comonomer X can advantageously be obtained by copolymerization of the monomers (first comonomer, optional second comonomer, and optionally the functional monomer). This polymerization can be carried out by means of a high-pressure free-radical process or a solution process, in an autoclave or tubular reactor, these processes and reactors being well known to those skilled in the art.

According to another embodiment, when the functional monomer X is not copolymerized in the polymer chain, for example polyolefin chain, it can be grafted onto said polymer chain, for example polyolefin chain. The grafting is also an operation known to those skilled in the art. The case where several different functional monomers are copolymerized and/or grafted onto the polymer chain, for example polyolefin chain, would not depart from the context of the present invention.

It is of course possible to use blends of two or more polymers comprising one or more units resulting from the copolymerization and/or grafting of one or more comonomer(s) X described above, for instance blends of (co)polyolefins with polyolefins comprising at least one unit originating from a comonomer X. Such compatibilizing polymers are known and described, for example, in patents FR 2 291 225 and EP 0 342 066.

In the case where the polymer(s) of the polymer layer (1) is a biorenewable and/or biodegradable copolyester, the coextrusion tie(s) or compatibilizing agent(s) can, for example, be such as those described in patent WO 2008/149019.

The method b) previously indicated for improving the adhesion between the layer (1) and the layer (2) uses a compatibility or coupling layer (C) inserted between two noncompatible layers.

This layer (C) can also be understood to be a coextrusion tie when the first two layers (1) and (2) are prepared by extrusion.

This layer (C) which enables compatibility between the layers (1) and (2) can advantageously be a polymer layer. The polymers which provide compatibility between polyolefins and polyamides are well known to those skilled in the art and can, for example, be chosen from copolymers of olefin(s) and of monomers X as defined above, for example polyolefins grafted with (meth)acrylic acids or esters, and in particular chosen from:

polyethylene, polypropylene, ethylene/α-olefin copolymers, for example ethylene/propylene copolymers, ethylene/butene copolymers, all these products being grafted with unsaturated carboxylic acid anhydrides such as, for example, maleic anhydride or glycidyl methacrylate, ethylene/alkyl (meth)acrylate/maleic anhydride copolymers, the maleic anhydride being grafted or copolymerized, ethylene/vinyl acetate/maleic anhydride copolymers, the maleic anhydride being grafted or copolymerized, ethylene/alkyl (meth)acrylate/glycidyl methacrylate copolymers, the glycidyl methacrylate being grafted or copolymerized, ethylene/vinyl acetate/glycidyl methacrylate copolymers, the glycidyl methacrylate being grafted or copolymerized, copolymers of ethylene/(meth)acrylic acid, optionally salts thereof, polyethylene, propylene or ethylene/propylene copolymers, these polymers being grafted with a product which has a site that is reactive with amines, for instance maleic anhydride, epoxy, and the like, these grafted copolymers being subsequently condensed with polyamides or polyamide oligomers having a single amine end, for example with monoamino oligomers of caprolactam, as described, for example, in patents U.S. Pat. No. 5,070,145 and EP 0 564 338, blends of one or more of these polymers and/or copolymers.

As indicated above, such compatibilizing polymers are known and described, for example, in patents FR 2 291 225 and EP 0 342 066.

The layer (C) can optionally comprise at least one photocatalyst, of nature and in an amount identical to those described above for the polymer layer (1). The amount of said at least one photocatalyst included in the layer (C) may, however, be lower than that present in the polymer layer (1). The incorporation of said at least one photocatalyst into the polymer layer (C) can be carried out according to any method known to those skilled in the art, and in particular according to the method described above for the incorporation of said at least one photocatalyst into the polymer layer (1).

All these constituent films of the multilayer film according to the present invention can be manufactured according to any technique known to those skilled in the art, and for example according to the usual techniques of extrusion, of coextrusion of sheaths, extrusion and co-extrusion of cast films, and the like, using one or more extruders.

As a variant, the compatibilizing polymer(s) described above can be incorporated into the layer (1) or into the layer (2) or else into both the layers (1) and (2) previously defined.

In the above cases, the amount of compatibilizing polymer is the amount sufficient for it to be possible for the polymers of the layers (1) and (2) to be assembled into a film having the barrier properties and the mechanical properties mentioned above. This amount depends on the reactive groups contained in the polyolefin and in the compatibilizing polymer itself. Those skilled in the art can easily determine this amount. By way of example, this amount may be from 5 to 20 parts of compatibilizing polymer, per 100 parts by weight of polymer of layer (1) and of polymer of layer (2).

Preferably, the mixture of polymer of layer (1) and/or of polymer of layer (2) with the compatibilizing polymer is in the form of a polymer matrix of the nodules of polymer (used to prepare the layer (1) and/or the layer (2)) or of a blend of said polymers. These polymer blends are manufactured according to the usual techniques of melt blending (twin-screw, Buss, single screw), and other methods well known to those skilled in the art.

By virtue of the compatibilizing polymer, in the form of an intermediate layer (C) or incorporated into the layer (1) and/or the layer (2), it is thus possible to obtain adhesions greater than approximately 3 N/15 mm. By way of example, the thickness of the compatibilizing polymer layer (C) can be advantageously between 2 μm and 15 μm.

The various polymers and/or copolymers constituting the multilayer films according to the invention can also contain one or more additives known to those skilled in the art, chosen from antioxidants, UV-protecting agents, processing agents, agents for preventing extrusion defects, antifogging agents, antiblocking agents, antistatic agents, nucleating agents and colorants. These agents can be added to one or more of the constituent layers of the films of the present invention, according to techniques and in weight proportions well known to those skilled in the art.

In particular, the photocatalytic films of the present invention can comprise one or more organic and/or inorganic agents for protection against ultraviolet radiation. This is because the films of the invention are intended to be exposed to solar radiation for long periods and are thus liable to be degraded under the effect of ultraviolet (UV) radiation. If they are not protected, this degradation results in a plastic film which becomes opaque and friable. According to one preferred embodiment, the photocatalytic films of the present invention comprise, in addition to the photocatalyst nanoparticles, at least one agent for protecting against degradation due to UV radiation, the most well known and commonly used of which is $TiO_2$ in its nonphotocatalytic form, preferably transparent to visible radiation (400 nm to 800 nm), but which must act as a barrier to UV radiation (280 nm to 400 nm), i.e. nonphotocatalytic $TiO_2$.

As agent for protecting against UV radiation, it is consequently possible to use nonphotocatalytic particles, for instance $TiO_2$ of micronic size (pigment), or nanometric (photocatalytic) $TiO_2$, or any other photocatalyst, the photocatalytic effect of which is inhibited, for example, by coating said particles. Such particles of which the photocatalytic effect has been inhibited but which have protective properties against UV radiation are, for example, $TiO_2$ coated with a film of $SiO_2$ or $Al_2O_3$ or $ZrO_2$ or other metal oxides. This treatment makes it possible to go from a photocatalytic activity of 6.01 mol/gh for an uncoated submicronic $TiO_2$ to 0.11 mol/gh for a submicronic $TiO_2$ coated with a film of metal oxide, which is similar to coated rutile used as a pigment (0.07 mol/gh) and much lower than pigment anatase (0.87 mol/gh) (see "Handbook of Fillers", ChemTec, 3rd Edition, (2010), page 148).

The use of $TiO_2$ as pigment is known to give plastic mulch films the opacity and the white color. The pigment $TiO_2$ will have a maximum opacity with respect to the desired color if the diameter of the particles of which it is composed is equal to half the wavelength of said desired color. For example, for a blue-green light to which the eye is the most sensitive, the average wavelength is 460 nm, and therefore a particle diameter of 230 nm will give the maximum opacity with respect to visible radiation.

For this application, use is advantageously made of rutile $TiO_2$ which has the highest refractive index and which is 2.75. Use will, for example, be made of the rutile titanium dioxide Ti-Pure® R-105 from DuPont or of the rutile-based Sachtleben® R 620 K from Sachtleben having an average crystal size of 210 nm. These white plastic films have no photocatalytic activity and can remain on a field for more than a year without degradation due to UV radiation.

Another advantage of the photocatalytic films of the present invention lies in the fact that they comprise at least one photocatalytic agent, optionally in combination with at least one agent for protecting against radiation, depending on whether it is desired for the film not to be degraded by UV radiation or to be weakly degraded or slowly degraded by said UV radiation. It is therefore possible to prepare photocatalytic films which comprise both a photocatalyst, for example Aeroxide® $TiO_2$ P25 from Evonik, and a protective white pigment, such as Ti-Pure® R-105 from DuPont or Sachtleben® R 620 K from Sachtleben. Aeroxide® $TiO_2$ P25 is not used as a white pigment for coloring the plastic films because the size of its particles is too small to refract the visible light spectrum and therefore to give a homogeneous and opaque white color.

The respective amounts of photocatalyst and of agent for protecting against UV radiation will be adjusted by those skilled in the art according to the photocatalytic effect desired and the duration of protection of the film desired, in particular according to the duration of the fumigation treatment envisioned, to the atmospheric and edaphic conditions and to the duration and the amount of sunshine observed on the soils and agricultural substrates to be treated.

According to one variant of the invention, the photocatalytic films can also comprise one or more "reinforcing" polymer layers (3), placed above and/or below the polymer layer (1) or the polymer layers (1) and (2) or else inserted between the layers (1) and (2).

These reinforcing layers make it possible to further reinforce the structure of the photocatalytic film. Of course, a reinforcing layer placed below the other layer(s) will have to be permeable to the vapors of the fumigant, whereas the reinforcing layer placed above the other layer(s) will have to be permeable to UV radiation, and advantageously impermeable to the vapors of the fumigant.

The nature of these reinforcing layers may be of any type known to those skilled in the art, and these layers can in particular comprise one or more of the polymers defined for the polymer layers (1) and (2) previously defined. It should be understood that the adhesion of the reinforcing layer(s) (3) can be improved by incorporating at least one compatibilizing agent into the layer(s) (3), or else said layers can be coextruded with a compatibility polymer, as previously described.

According to yet another variant, the invention relates to films for fumigation as have just been described and which also comprise one or more colored layers. As previously mentioned, the plastic films or sheets commonly used on soils or cultivation substrates may need to be colored, depending on whether it is desired to benefit from the air or soil temperature, to retain a certain degree of moisture, or the like.

The films of the present invention can thus comprise a colored additional layer (4), which is white, black, or any other color defined according to the needs and the climatic and edaphic conditions. This colored additional layer, which may be barely permeable or even impermeable to UV radiation, forms the lower part of the film according to the invention, i.e. the colored layer must be on the side of the soil or of the substrate.

In addition, and in order for it to be possible for the fumigant to reach the active layer, which is the polymer layer (1) comprising the photocatalyst, the colored layer must be permeable to said fumigant. Thus, the colored layer is a polymer layer advantageously consisting of the same polymer(s) as that(those) used for the polymer layer (1), said colored (or pigmented) layer also comprising at least one colorant (or pigment) of which the color and the amount depend on the desired final color of the multilayer film according to the present invention.

The colored layer (4) can optionally comprise at least one photocatalyst, of nature and in an amount which are identical to those described above for the polymer layer (1). When the colored layer (4) comprises at least one photocatalyst as indicated above, this colored layer (4) can thus act on the fumigant vapors, just like the polymer layer (1) and it can therefore be envisioned to eliminate photocatalytic film according to the invention. The incorporation of said at least one photocatalyst into the colored layer (4) can be carried out according to any method known to those skilled in the art, and in particular according to the method described above for the incorporation of said at least one photocatalyst into the polymer layer (1).

Moreover, in the case where the colored layer and the adjacent layer are not compatible with one another, it is possible to improve the adhesion between these two layers by using a compatibilizing agent or a compatibility layer, according to one of the two solutions a) and/or b) previously described.

The colored films are either commercially available or are easily obtained according to processes known to those skilled in the art, for example by introducing pigment(s) into the polymer matrix. The multilayer film according to the invention can thus have a total thickness of, for example, between 10 µm and 300 µm and preferably between 20 µm and 150 µm:

The multilayer film according to the invention can be put down on the soil either before carrying out the injection of fumigant(s), or immediately after this injection. It is recommended, if the film is put down before injection, not to damage the film with the injectors, and to provide for a leaktight system, for example by superposition and adhesive bonding of the strips of films, and/or by burying the edges of films in the earth, and/or any other techniques known to those skilled in the art.

The photocatalytic films according to the invention exhibit, in addition to good mechanical strength and gas-barrier effect properties, the ability to photocatalyze the fumigants which are imprisoned between the soil or substrate and said film. This photocatalysis allows decomposition, by virtue of ultraviolet radiation, for example the sun, lamps used in greenhouses and the like, of the often toxic and/or malodorous organic compounds which are used for the fumigation of said soils and substrates.

By virtue of the photocatalytic films of the present invention, it is possible to use fumigants of any type which are known to those skilled in the art, chosen from nematicides, herbicides, fungicides, insecticides and bactericides, for example those listed in the Pesticide Manual, Tenth edition, ed. Clive Tombin). In the present invention, the term "fumigant" is intended to mean any type of phytosanitary compound which complies at the same time with at least the following two essential conditions: (i) not having, at the doses at which it is active, any phytotoxicity on the crops put in place after the treatment and (ii) having the essential and rare property of not being completely absorbed in the soils or substrates for cultivation and of rapidly diffusing, in gas form, within the thickness of the soil to be treated, since phytopathogenic organisms are often up to 50 centimeters at least below the surface of said soil or of said substrate. Furthermore, for obvious productivity reasons, and also in order to limit the risk of further infestation, the treatment time during which the fumigant acts must be as short as possible.

By way of nonlimiting examples of fumigants, mention may be made of methyl bromide, methyl iodide, methyl isothiocyanate (MITC), 1,3-dichloropropene, chloropicrin, sulfuryl fluoride ($SO_2F_2$), phosphine, tetrathiocarbonate or other MITC-generating compounds, for instance Metam-sodium and Dazomet, and also certain sulfur-containing compounds, such as alkyl sulfides, dialkyl disulfides, dialkyl polysulfides, thiosulfinates and the like, and also mixtures of two or more of them in any proportions.

All these fumigating compounds are known and widely described in the literature. International application WO 2002/074083 describes in particular fumigants based on sulfur-containing compounds, and in particular the compounds corresponding to general formula (I)

$$R-S(O)_n-S_x-R' \qquad (I)$$

in which R is chosen from alkyl and alkenyl radicals containing from 1 to 4 carbon atoms, n is equal to 0, 1 or 2, x takes the values ranging from 0 to 4, limits included, and R' is chosen from alkyl and alkenyl radicals containing from 1 to 4 carbon atoms or, only when n=x=0, R' can represent a hydrogen atom or an alkali metal atom.

The fumigants mentioned above, alone or as mixtures, and in particular those of formula (I) above, are quite particularly suitable for the fumigation of soils or substrates, in joint use with the photocatalytic films previously described, because they meet three essential conditions for being able to be used practically in soil or substrate disinfection: they exhibit overall pesticidal properties (nematicidal, fungicidal, herbicidal, insecticidal, bactericidal); they are capable of diffusing rapidly within the thickness of the soil to be treated; and they result in a concentration of gas sufficient to kill the phytopathogenic organisms present.

Among the fumigants known today, those corresponding to formula (I) above are preferred for the needs of the present invention. Indeed, as substitutes for methyl bromide, the compounds of formula (I) are all the more advantageous since some are already present in nature, originating from the natural degradation of cruciferous plants and alliums. In particular, thiosulfinates, included in general formula (I), are products that are naturally given off when alliums are milled and, in this respect, can be used in organic agriculture.

Furthermore, the compounds of formula (I) do not contain halogen atoms that generate halogenated radicals responsible for the catalytic destruction of stratospheric ozone, the compounds of formula (I) present no danger to the ozone layer. As nonlimiting examples of R and R' radicals, mention may be made of methyl, propyl, allyl and 1-propenyl radicals.

Among the compounds of formula (I), preference is given to those for which n=0, i.e. the compounds corresponding to formula (I'):

in which R and R', which may be identical or different, preferably identical, each represent, independently of one another, an alkyl or alkenyl, preferably alkyl, radical containing from 1 to 4 carbon atoms, and x represents 1, 2, 3 or 4.

Other preferred compounds are disulfides (n=0, x=1) and more particularly dimethyl disulfide (DMDS).

The fumigants described above, and in particular the compounds of formula (I) described above, can be used in the pure state or in various forms, for example in aqueous, organic or aqueous-organic emulsions or microemulsions, in the form of an emulsifiable concentrate, in the form of products which are microencapsulated, nanoencapsulated or supported by a solid, in aqueous, organic or aqueous-organic solutions, or else as a mixture with one or more products having activity for the treatment of soils or substrates.

All the formulations defined above can be prepared according to methods well known to those skilled in the art. Thus, for example, the aqueous emulsions and the microemulsions can be obtained by adding one or more surfactants to the fumigating compound, and then by adding to the mixture obtained a certain amount of water so as to obtain a stable emulsion or a microemulsion.

More particularly suitable for the preparation of the aqueous emulsions or the microemulsions are surfactants with a predominantly hydrophilic nature, i.e. those having an HLB (Hydrophilic Lipophilic Balance) greater than or equal to 8, which may be of anionic, cationic, nonionic or amphoteric nature.

As nonlimiting examples of anionic surfactants, mention may be made of the alkali metal, alkaline-earth metal, ammonium or triethanolamine salts of alkyl-, aryl- or alkylarylsulfonic acids, of fatty acids of basic pH, of sulfosuccinic acid or of alkyl, dialkyl, alkylaryl or polyoxyethylenealkylaryl esters of sulfosuccinic acid. Mention may also be made of the alkali metal or alkaline-earth metal salts of esters of sulfuric, phosphoric, phosphonic or sulfoacetic acid and of saturated or unsaturated fatty alcohols, and also the alkoxylated derivatives thereof. Other further surfactants are represented by the alkali metal or alkaline-earth metal salts of alkylarylsulfuric, alkylarylphosphoric or alkylarylsulfoacetic acids, and also the alkoxylated derivatives thereof.

The cationic surfactants that can be used are, for example, those of the family of quaternary alkylammoniums, of sulfoniums or of fatty amines at acid pH, and also the alkoxylated derivatives thereof. As nonlimiting examples of nonionic surfactants, mention may be made of alkoxylated alkyl phenols, alkoxylated alcohols, alkoxylated fatty acids, fatty esters of glycerol or fatty derivatives of sugar.

The amphoteric surfactants that can be used are, for example, alkylbetaines or alkyltaurines. The surfactants that are preferred for the preparation of the aqueous emulsions and of the microemulsions are compounds based on alkyl benzenesulfonate and on alkoxylated alkyl phenol.

For the formulations of fumigant(s) in solution form, the organic solvents that can be used are hydrocarbons, alcohols, ethers, ketones, esters, halogenated solvents, mineral oils, natural oils and derivatives thereof, and also aprotic polar solvents such as dimethylformamide, dimethyl sulfoxide or N-methylpyrrolidone. Biodegradable solvents, and more particularly methyl esters of rapeseed oils, are particularly suitable.

According to one variant of the present invention, two or more fumigants can be used, jointly, as a mixture, alternately or sequentially. In particular, use may be made of two or more fumigants having complementary or synergistic activities, chosen from 1,3-dichloropropene, sulfuryl fluoride ($SO_2F_2$), phosphine, methyl iodide, chloropicrin ($Cl_3C$—$NO_2$), Metam-sodium ($CH_3$—$NHCS_2Na$), sodium tetrathiocarbonate ($Na_2CS_4$), MITC($CH_3$—NCS), Dazomet (MITC generator), and the compounds of formula (I), in particular dialkyl disulfides, for example DMDS.

In the context of the present invention, i.e. in combination with the photocatalytic films, the fumigants and the compositions containing them can be applied according to any one of the conventional methods for introducing pesticides into the soil, for instance injection using colters, which enables deep introduction of the product, spraying onto the soil, drip via a conventional irrigation system, or "sprinkler" type sprinkling. After introducing the fumigating product(s) into the soil or the cultivation substrate, it is possible to perform spraying, for example using a rotary spade in the case of injection into the soil.

The doses of fumigant(s) generally applied in order to obtain the desired effect are generally between 150 g/ha and 1000 kg/ha, preferably between 1 kg/ha and 750 kg/ha, and depend on the nature of the fumigant(s) used, on the degree of soil infestation, on the nature of the pests and of the phytopathogenic organisms, on the type of crop and of soil or substrate, and on the methods of application.

At the doses indicated above, the desired general pesticidal (at the same time nematicidal, fungicidal, herbicidal, insecticidal and bactericidal) effect is observed and no phytotoxic effect, or only a negligible one, is observed. Combining the treatment using a compound of formula (I) with a (simultaneous or nonsimultaneous) treatment with one or more other pesticidal, insecticidal and/or fungicidal substances and/or with a fertilizer would not be a departure from the context of the present invention.

The present invention also relates to the use of the photocatalytic films, as have just been described, in processes for fumigating soils or substrates intended for crops, in particular for market garden and horticultural crops, such as, for example and in a nonlimiting manner, strawberries, lettuces, tomatoes, melons, cucumbers, aubergines, carrots, potatoes, ornamental flowers, and the like.

The films of the present invention can also be used on soils, substrates or more simply items which are not necessarily intended for crops, but which suffer fungal infestations and/or infestations by insects, nematodes, and other insects, larvae, nits, which are harmful. The possible uses are, for example, in the fields of the storage of wood, hay, straw, cereals, and more generally any food or non-food product capable of being degraded by fungi, insects, larvae, nematodes and the like.

A subject of the invention is also a fumigation treatment kit comprising at least one photocatalytic film as previously described, and at least one fumigant, preferably at least one sulfur-containing volatile organic compound, preferably of formula (I) or of formula (I'), said fumigant more preferably being dimethyl disulfide.

Another subject of the present invention is a process for fumigating a soil, a cultivatable substrate or an item, comprising at least the following steps:
a) application in said soil, substrate or item, and/or at the surface of said soil, substrate or item, of at least one fumigant, as has just been defined;
b) total or partial coverage of said soil, substrate or item with a photocatalytic film, as previously defined, before or after step a);
c) exposure of said photocatalytic film to ultraviolet radiation, for a period of time which can range from a few days to several weeks; and
d) optional total or partial removal or simple perforation of said photocatalytic film.

In the process described above, the possibility of injecting at least one fumigant between the film and the substrate is thus envisioned.

In step d) of the above process, the film according to the invention can be removed, when it is considered that the fumigant(s) has (have) performed its (their) role. By virtue of the photocatalyst, the fumigant(s) is (are) at least partially or even totally degraded and the removal of the film causes only little or even no harm to either the handler or to the environment.

As a variant, the film may be only partially removed, or may even remain in place. In the latter case, the film can be perforated in one or more predefined places, where the crops, such as the transplants for example, will be planted.

The injection of the fumigant(s) into the soil can be carried out according to any technique known to those skilled in the art, and for example as previously described.

The photocatalytic film can be deposited on the soil, substrate or item before or after this fumigation step, for example by simply unrolling the film on said soil, substrate or item. It is advisable to ensure satisfactory leaktightness, for example by burying the edges of the film, in order to avoid any leaking of the fumigant into the atmosphere, the fumigant having to be retained, during the required fumigation time, between the soil, substrate or item and the photocatalytic film.

The photocatalytic effect is provided by exposure to ultraviolet radiation, for example direct sunlight or else by means of ultraviolet radiation lamps, used for example for crops in greenhouses.

The effect of the ultraviolet radiation is the photocatalytic action of the particles of photocatalyst(s) which degrades the vapors of the fumigant(s) which are given off from the soil or substrate treated. After photocatalytic destruction of the vapors of the fumigant(s), the plastic films can be totally or partially removed from the soils or substrates so as to allow planting of the crops in the soils thus treated by fumigation.

Another advantage of the fumigation process of the invention using the photocatalytic films as have just been defined lies in the fact that the products of photocatalytic degradation of the fumigants can be useful for the growth of the crops.

This is because some fumigants can be decomposed, under the effect of the ultraviolet radiation and of the photocatalyst, into mineral products that are useful for the growth of crops. This is in particular the case with the fumigating compounds containing sulfur, and more particularly with the fumigants of formula (I) defined above, and quite particularly dialkyl disulfides, such as DMDS for example, which are decomposed by photocatalysis into various sulfur oxidation products, until sulfates are formed.

Sulfates are well-known crop fertilizers. Thus, the fumigation process according to the invention, using at least one fumigant comprising at least one sulfur atom, for example at least one fumigant of formula (I), for example DMDS, and a photocatalytic film as previously defined, makes it possible not only to effectively treat the phytopathogens present in crop soils and substrates but also to provide fertilizer which is useful for the growth of said crops.

The figures appended to the present description illustrate some exemplary embodiments of the invention, without, however, limiting the scope of said invention.

FIG. 1 represents diagrammatically a film for fumigation according to the invention, comprising a polymer layer (1) loaded with photocatalyst. This polymer layer (1) is placed above a substrate (S) and is irradiated by solar radiation. This polymer layer (1) is permeable to solar UV radiation which activates the photocatalyst. The fumigant vapors are represented by the dashed arrows. These vapors can cross the polymer layer (1), which is permeable to said fumigant vapors, and come into contact with the photocatalytic particles. The fumigant is thus photocatalyzed before being able to completely cross the polymer layer (1).

Figure 2:
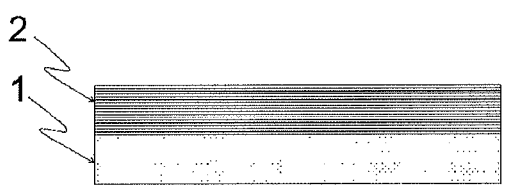
FIG. 2 represents a photocatalytic film comprising a first polymer layer loaded with photocatalyst particles, and a second polymer layer.

FIG. 2 represents a variant of a photocatalytic film according to the invention, comprising:
a polymer layer (1) loaded with photocatalyst particles, which is permeable to the fumigant vapors and permeable to UV radiation, and
a polymer layer (2) which is impermeable to the fumigant vapors and permeable to UV radiation.

Figure 3:
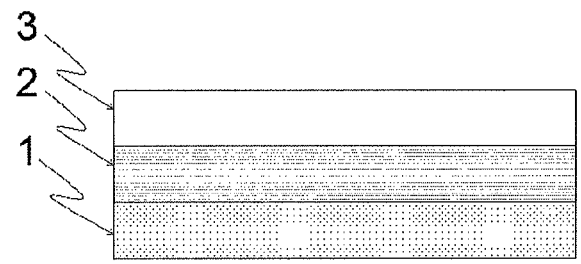
FIG. 3 represents a photocatalytic film comprising a first polymer layer and a second polymer layer, and also a reinforcing polymer layer.

FIG. 3 represents another variant of a photocatalytic film according to the invention, comprising a polymer layer (1) and a polymer layer (2) as indicated in FIG. 2, and also a reinforcing polymer layer (3), this polymer layer (3) being itself permeable to UV radiation.

Figure 4:
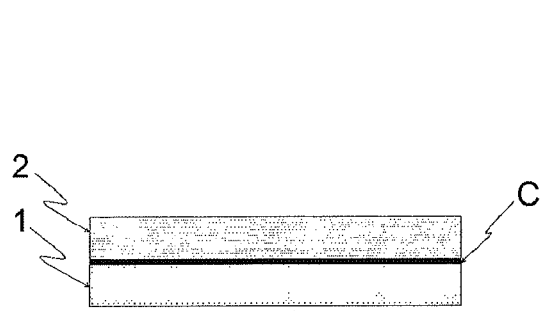
FIG. 4 represents a photocatalytic film comprising a first polymer layer and a second is polymer layer, and also a compatibility layer.

FIG. 4 represents yet another variant of a film according to the invention, comprising a polymer layer (1) and a polymer layer (2) as indicated in FIG. 2, and also a compatibility layer (C) as defined above.

Figure 5:
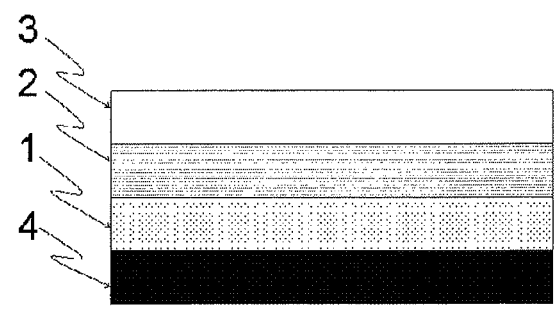
FIG. 5 represents a photocatalytic film comprising a first polymer layer, a second polymer layer, a reinforcing polymer layer, and also a colored polymer layer.

FIG. 5 also represents a variant of a photocatalytic film according to the invention, comprising a polymer layer (1), a polymer layer (2), a polymer layer (3), as indicated in FIG. 3, and also a colored polymer layer (4), this polymer layer (4) being itself permeable to the fumigant vapors. The fumigant vapors cross the polymer layer (4) and reach the active polymer layer (1) where the fumigant vapors come into contact with the photocatalyst particles subjected to the UV radiation which has passed through the polymer layers (2) and (3).

The examples below illustrate the invention without, however, limiting the scope thereof defined by the appended claims.

EXAMPLE 1

Preparation of a Polyethylene Film Loaded with Photocatalytic $TiO_2$ a) Preparation of the Master-Batch A microextruder, DSM Research model micro 15 twin-screw, is used. The chamber has a capacity of 15 ml with six heating zones (maximum temperature: 350° C.) and a rotational screw speed which can range from 1 to 250 revolutions per minute. Cooling can be carried out under air or with a water circuit.

The polyethylene used is an LDPE (linear low-density polyethylene) with a melt flow index (MFI) of 1 g/10 min (190° C./2.6 kg) in the form of granules, which is sold by Aldrich (reference: 428078). The titanium dioxide in powder form is Aeroxide® $TiO_2$ P 25 from Evonik.

A master-batch is prepared, in the microextruder, at a temperature of 235° C., for an average melt temperature of approximately 224° C., with the speed of the two co-rotating screws set at 200 revolutions per minute. The blending time after stabilization of the "couple" is 5 minutes.

14 g of a 70/30 LDPE-$TiO_2$ master-batch are thus prepared by mixing 9.8 g of LDPE and 4.2 g of $TiO_2$. A rod 3 mm in diameter is obtained at the extruder outlet. This master-batch is subsequently denoted MB1.

b) Preparation of the PE/$TiO_2$ Film

The operating conditions are identical to those of the preparation of the master-batch, namely: working temperature 235° C., average melt temperature: approximately 224° C., speed of the two co-rotating screws set at 200 revolutions per minute, blending time after stabilization of the "couple": 5 minutes.

10 g of a PE polymer film containing 10% by weight of titanium dioxide are thus prepared from a mixture of 6.67 g of LDPE and 3.33 g of the master-batch prepared in step a). At the outlet of the microextruder, the mixture is in the form of a rod.

To obtain a film of which the average thickness is 500 µm, from the previously manufactured rod, a press is used, with a working temperature of 150° C., a pressing time of 30 seconds, and a pressing pressure of $10^7$ Pa. To obtain a film of which the average thickness is 50 µm, from the previously manufactured rod, the rod is drawn out according to the conventional techniques known to those skilled in the art, for example according to the cast film extrusion technique.

Films are prepared on a 3-layer laboratory line from Dr Collin, equipped with 3 extruders and a spiral mandrel die (50 mm in diameter). The symmetrical coextruded structure is the following:
- 15 µm PE layer (LDPE 2200TC00 from Sabic), containing 15% of a PE-based coupling agent (Orevac® OE825), the extrusion temperature is set at 220° C.;
- 15 µm PA6 layer (Durethan® C38F), the extrusion temperature is set at 230° C.;
- 15 µm PE layer (LDPE 2200TC00 from Sabic), this layer contains 15% of master-batch MB1 and 15% of a PE-based coupling agent (Orevac OE825), the LDPE-based master-batch MB1 (d~918, MI=1) containing 30% of nanometric titanium dioxide (Aeroperl® P25/20 from Evonik) was prepared beforehand by twin-screw compounding according to the rules known to those skilled in the art; the extrusion temperature is 220° C.

The temperature of the die is set at 230° C., the die gap is adjusted to 1.2 mm, the degree of swelling to 2.5 and the line speed at 5 m/min. The film obtained has a width of 200 mm. The adhesion measured at the PE/PA6 interface is 10 N/15 mm. The test is carried out using a T-peeling test at 200 mm/min.

EXAMPLE 2

The effectiveness of the various types of films is tested with DMDS in a 0.35 l leaktight Pyrex reaction vessel which is transparent to UV radiation, with a relative humidity of 90% and at a temperature of 45° C., so as to reproduce the actual conditions in the field. The film is blocked between the walls and the upper window of the reaction vessel, the active layer being oriented toward the bottom of the reaction vessel. The film is irradiated from above through the Pyrex window.

The solar illumination is provided by virtue of a 150 watt Newport solar simulator, equipped with a xenon lamp, without ozone, the light intensity of which is adjusted to 1 sun. The distance between the Pyrex window of the reaction vessel and the lamp can be adjusted in order to control the irradiation power. An Oriel 91150 calibration solar cell makes it possible to determine the amount of light in "sun" units for the solar simulator. With this simulator, all the tests are carried out with one (1) "sun", equivalent to 1000 $W.m^{-2}$ (100 $mW.cm^{-2}$) at 25° C. The area irradiated is 28 $cm^2$.

The concentration of DMDS and of carbon dioxide ($CO_2$) was automatically monitored every 10 minutes by gas chromatography (Varian® 4900 chromatograph), the chromatograph being equipped with a TCD detector and with 2 chromatographic columns (CP-SiI5CB for the DMDS and Porapak® for the $CO_2$).

Water-free and $CO_2$-free synthetic air is introduced into the reaction vessel. The DMDS and the water are introduced into the reaction vessel with a microsyringe through a septum. All the tests are carried out in parallel, on the one hand with irradiation and, on the other hand, without irradiation (in the dark). The test without irradiation corresponds to the control test.

Test 1: Test on Polyethylene Film

The film tested is a monolayer film of polyethylene (PE) 50 µm thick and loaded with 1.3% by weight of $TiO_2$, under a relative humidity of 86%, at a temperature of 45° C. and a DMDS concentration of 10114 ppmv. A linear decrease in the DMDS concentration of 30% is measured after 6 days of irradiation.

Test 2: Test on Transparent VIF-$TiO_2$ Films

For this test, a three-layer film (according to FIG. 3) having a total thickness of 45 µm consisting of the following is used:
i) a PE film having a thickness of 15 µm, permeable to gases and to UV radiation, loaded with 3.3% by weight of $TiO_2$, this film being in contact with the bottom of the measuring cell;
ii) a layer impermeable to gases and permeable to UV radiation; and
iii) a reinforcing layer permeable to UV radiation.

After introduction of DMDS under the film and irradiation with UV radiation, a linear decrease in the concentration of DMDS is noted. After 50 hours of irradiation, the concentration of DMDS decreased by close to 25%.

Test 3: Tests on Transparent VIF-TiO$_2$ Films

The film used in test 2 is used in a further test. The temperature of the test is set at 45° C., the relative humidity is 90%, and the initial concentration of DMDS is 25500 ppmv. The test is carried out this time with an irradiation equivalent to 1.9 suns. A more rapid decrease in the residual concentration of DMDS under the film is noted with 1.9 suns compared with 1 sun. This result clearly shows the photocatalytic effect of the films.

Moreover, the concentration of carbon dioxide (CO$_2$) is monitored. After 60 hours of irradiation, the concentration of CO$_2$ measured under the film makes it possible to deduce a mineralization of 10% of the DMDS. This demonstrates once more the photocatalytic properties of the film tested.

Test 4: Tests on Transparent VIF-TiO$_2$ Films

Tests are carried out with a VIF-TiO$_2$ film having a total thickness of 80 µm, containing 3.3% of TiO$_2$ in the active layer of PE which is 50 µm thick. The conditions are: 1.9 suns, 90% relative humidity, temperature: 45° C., concentration of DMDS: 25500 ppmv.

The concentration of carbon dioxide is measured, which makes it possible to deduce a degree of mineralization of 21% after 60 hours of irradiation. These results show that, with a film having the same TiO$_2$ load of 3.3%, but with a greater thickness (15 µm compared with 50 µm in this test), the degree of mineralization increases significantly.

These tests show that the photocatalytic activity is variable according to the thickness of the film; the thicker the film, the greater the photocatalytic activity at a constant level of photocatalyst load.

Test 5: Tests on Transparent VIF-TiO$_2$ Films

Tests are again carried out as described in test 4 above; this time using a VIF-TiO$_2$ film having a total thickness of 80 µm, loaded with 1.3% by weight of TiO$_2$ for an active layer of PE having a thickness of 50 µm. The relative humidity is 90%, the temperature is 45° C. and the concentration of DMDS is 25500 ppmv.

The degree of mineralization, deduced after measuring the CO$_2$ formed after 60 hours of irradiation, is 11%. These tests show that the photocatalytic activity is directly linked to the concentration of photocatalyst present in the active layer of the film.

Test 6: Tests on Transparent VIF-TiO$_2$ Films

VIF/TiO$_2$ film (film prepared with an Orevac®-TiO$_2$ master-batch), relative humidity: 90%, temperature: 45° C., amount of TiO$_2$: 4.5%, film having a total thickness of 45 µm, including 15 µm for the active PE layer, concentration of DMDS: 32 mg.l$^{-1}$.

The photocatalysis of the DMDS is rapid and the formation of CO$_2$ is already observed after 20 hours of irradiation. The CO$_2$ concentration increases up to 3000 ppmv after 60 hours and corresponds to 12% mineralization of the DMDS.

This film prepared with the Orevac®-TiO$_2$ master-batch enables a rapid decrease in the concentration of DMDS.

All these results clearly demonstrate the capacity of the TiO$_2$-doped films to photocatalytically oxidize DMDS under solar irradiation.

Test 7: Test on Colored (Black or White) VIF-TiO$_2$ Films

The film tested here is a 4-layer film: layer 1: LDPE of 15 µm; layer 2: polyamide-6,6 of 15 µm; layer 3: LDPE of 15 µm; and layer 4: LDPE with white pigment (micrometric pigmentary TiO$_2$) of 5 µm. Only the PE layer, which is above the colored layer (layer 1), contains the photocatalytic TiO$_2$.

A white-colored film, having a total thickness of 45 µm, the active layer of which is an LDPE layer of 15 µm, loaded with 3.3% TiO$_2$, under a relative humidity of 90%, at a temperature of 45° C., and a concentration of DMDS of 31 mg.l$^{-1}$, is tested.

The concentration of DMDS decreases by 1030 ppmv, while the formation of CO$_2$ is approximately 485 ppmv in 15 hours, which corresponds to a degree of mineralization of 16%.

This test demonstrates that it is possible to use photocatalytic films according to the invention which are colored, without impairing the photocatalytic efficiency of said films.

EXAMPLE 3 (COMPARATIVE)

Preparation of a Polyethylene Film Loaded with Anti-UV TiO$_2$

The polyethylene used is an LDPE (linear low-density polyethylene) with a melt flow index (MFI) of 1 g/10 min (190° C./2.6 kg) in the form of granules, sold by Aldrich (reference: 428078).

The anti-UV TiO$_2$ is the Light Stabilizer® 210 from DuPont. The TiO$_2$ crystals are coated with a layer of Al$_2$O$_3$ and the average particle diameter is 135 nm.

14 g of 97/3 LDPE-TiO$_2$ master-batch are prepared by mixing 13.58 g of LDPE and 0.42 g of Light Stabilizer 210 TiO$_2$ in a microextruder, at a temperature of 235° C., for an average melt temperature of approximately 224° C., with the speed of the two co-rotating screws set at 200 revolutions/minute. The blending time after stabilization of the "couple" is 5 minutes. A rod 3 mm in diameter is obtained at the extruder outlet.

This master-batch (3.33 g) is melt-blended with 6.67 g of LDPE, according to the protocol described in step b) of example 1, and the mixture is subsequently extruded in rod form. To obtain a monolayer film having an average thickness of 50 µm, the rod is drawn out according to the conventional techniques known to those skilled in the art, for example according to the cast film extrusion technique.

Test of the Polyethylene Film Loaded with Anti-UV TiO$_2$

This transparent polyethylene (PE) monolayer film 50 µm thick, loaded with 3% by weight of anti-UV TiO$_2$, is tested, according to the protocol described in example 2, under a relative humidity of 92% and at a temperature of 45° C. and a concentration of DMDS of 11052 ppmv. No decrease in the concentration of DMDS is measured after 6 days of irradiation, compared with the control test.

EXAMPLE 4 (COMPARATIVE)

Preparation of a Polyethylene Film Loaded with Pigmentary TiO$_2$

For this film, the procedure of example 3 is reiterated, with the anti-UV TiO$_2$ being replaced with TiO$_2$, sold by DuPont under the name Ti-Pure® R-105, which is SiO$_2$-coated, rutile-form, pigmentary TiO$_2$, the average particle size of which is 310 nm.

14 g of 97/3 LDPE-TiO$_2$ master-batch are prepared by mixing 13.58 g of LDPE and 0.42 g of Ti-Pure® R-105 TiO$_2$ in a microextruder, at a temperature of 235° C., for an average melt temperature of approximately 224° C., with the speed of the two co-rotating screws set at 200 revolutions/minute. The blending time after stabilization of the "couple" is 5 minutes. A rod 3 mm in diameter is obtained at the extruder outlet.

This master-batch (3.33 g) is melt-blended with 6.67 g of LDPE, according to the protocol described in step b) of example 1, and the mixture is then extruded in rod form. To obtain a monolayer film having an average thickness of 50 µm, the rod is drawn out according to the conventional techniques known to those skilled in the art, for example according to the cast film extrusion technique.

Test of the Non-Photocatalytic White Polyethylene Film

This white polyethylene (PE) monolayer film having a thickness of 50 µm and loaded with 3% by weight of pigmentary $TiO_2$ is tested, according to the protocol of example 2, under a relative humidity of 89% and at a temperature of 45° C. and a concentration of DMDS of 10645 ppmv. No decrease in the concentration of DMDS is measured after 6 days of irradiation, compared with the control test.

The invention claimed is:

1. A photocatalytic film comprising at least one first polymer layer comprising at least one photocatalyst, said at least one first polymer layer being both permeable to the vapors of at least one fumigating compound and permeable to ultraviolet radiation capable of activating the photocatalyst, wherein the at least one first polymer layer is a polymer film comprising at least one polymer A chosen from polyolefins and polyesters.

2. The photocatalytic film as claimed in claim 1, wherein the at least one photocatalyst is present in the form of particles having an average particle size of between 0.5 nm and 200 nm.

3. The photocatalytic film according to claim 2, wherein the at least one photocatalyst is present in the form of particles having an average particle size of between 0.5 nm and 100 nm.

4. The photocatalytic film according to claim 2, wherein the at least one photocatalyst is present in the form of particles having an average particle size of between 1 nm and 50 nm.

5. The photocatalytic film as claimed in claim 1, wherein the at least one polymer A is chosen from polyolefins resulting from the polymerization or from the copolymerization of olefins which are chosen from ethylene, propylene, 1-butene, and mixtures thereof.

6. The photocatalytic film according to claim 5, wherein said at least one polymer A is polyethylene.

7. The photocatalytic film as claimed in claim 1, wherein the at least one polymer A is chosen from biobased or biodegradable polylactides, poly(hydroxyalkanoates), poly(alkylene succinates), thermoplastic starches, and mixtures thereof.

8. The photocatalytic film as claimed in claim 1, wherein the photocatalyst is chosen from titanium dioxide, silicon dioxide, zinc oxide, tungsten trioxide, silicon carbide, iron II oxide or iron III oxide, cerium dioxide, zirconium dioxide, tin dioxide, zinc sulfide, cadmium sulfide, silicon carbide, and mixtures thereof in any proportions.

9. The photocatalytic film as claimed in claim 1, wherein the amount of photocatalyst is between 0.1% and 30% by weight of photocatalyst relative to the total weight of the at least one first polymer layer.

10. The photocatalytic film as claimed in claim 1, wherein the thickness of the at least one first polymer layer is between approximately 5 µm and approximately 100 µm.

11. The photocatalytic film as claimed in claim 1, also comprising at least one second polymer layer impermeable to the vapors of said at least one fumigating compound and permeable to ultraviolet radiation.

12. The photocatalytic film as claimed in claim 11, wherein the at least one second polymer layer is chosen from nitrogenous and/or oxygen-containing polar resins, polyesters and copolyesters, thermoplastic starches, and mixtures thereof in any proportions.

13. The photocatalytic film as claimed in claim 11, wherein the at least one second polymer layer is a polyamide or a copolyamide chosen from the products of condensation of one or more amino acids, of one or more lactams, and of one or more diamines with one or more diacids, and mixtures of these monomers.

14. The photocatalytic film as claimed in claim 11, further comprising one or both of:
at least one compatibilizing agent in the at least one first polymer layer (1), in the at least one second polymer layer (2), or in both the at least one first polymer layer (1) and the at least one second polymer layer (2); and
a compatibilizing polymer layer (C) between the at least one first polymer layer and the at least one second polymer layer.

15. The photocatalytic film as claimed in claim 1, further comprising one or more reinforcing layers, one or more colored layers, or one or more reinforcing layers and one or more colored layers.

16. The photocatalytic film as claimed in claim 1, wherein the total thickness of the photocatalytic film is between 10 µm and 300 µm.

17. A fumigation treatment kit comprising at least one photocatalytic film as claimed in claim 1, and at least one fumigant.

18. The photocatalytic film according to claim 1, wherein said polyolefins and polyesters are biobased, biodegradable, or biobased and biodegradable.

19. A process for fumigating a soil, a cultivatable substrate or an item, comprising at least the following steps:
a) applying in said soil, substrate or item, and/or at the surface of said soil, substrate or item, at least one fumigant, and
b) totally or partially covering said soil, substrate or item with a photocatalytic film, as claimed in claim 1, before or after step a),
c) exposing said photocatalytic film to ultraviolet radiation for a period of time; and
d) optionally totally or partially removing or perforating said photocatalytic film.

20. The fumigation process as claimed in claim 19, wherein the fumigant is chosen from methyl bromide, methyl iodide, methyl isothiocyanate (MITC), 1,3-dichloropropene, chloropicrin, sulfuryl fluoride ($SO_2F_2$), phosphine, tetrathiocarbonate or other MITC-generating compounds, alkyl sulfides, dialkyl disulfides, dialkyl polysulfides, thiosulfinates, and mixtures thereof in any proportions.

21. The process as claimed in claim 20, wherein the fumigant is chosen from the sulfur-containing volatile pesticidal compounds of general formula (I):

$$R-S(O)_n-S_x-R' \tag{I}$$

wherein R represents an alkyl or alkenyl radical containing from 1 to 4 carbon atoms, n is equal to 0, 1 or 2, x has a value from 0 to 4, limits included, and R' represents an alkyl or alkenyl radical.

22. The process as claimed in claim 21, wherein the fumigant is chosen from the sulfur-containing volatile pesticidal compounds of formula (I'):

$$R-S-S_x-R' \tag{I'}$$

in which R and R', which may be identical or different, each represent, independently of one another, an alkyl or alkenyl radical containing from 1 to 4 carbon atoms, and x represents 1, 2, 3 or 4.

23. The process as claimed in claim 22, wherein the fumigant is dimethyl disulfide.

* * * * *